US008443803B2

(12) United States Patent
Reisman (10) Patent No.: US 8,443,803 B2
(45) Date of Patent: May 21, 2013

(54) RESPIRATION BAG (75) Inventor: Ron Reisman, Ramat Hasharon (IL)

(73) Assignee: Micro BVM Ltd., Jerusalem (IL)

( * ) Notice: Subject to any disclaimer, the term of this patent is extended or adjusted under 35 U.S.C. 154(b) by 343 days.

(21) Appl. No.: 12/682,100

(22) PCT Filed: Oct. 7, 2008

(86) PCT No.: PCT/IL2008/001338
§ 371 (c)(1),
(2), (4) Date: Jun. 4, 2010

(87) PCT Pub. No.: WO2009/047763
PCT Pub. Date: Apr. 16, 2009

(65) Prior Publication Data
US 2010/0236557 A1 Sep. 23, 2010

Related U.S. Application Data (60) Provisional application No. 60/960,667, filed on Oct. 9, 2007.

(51) Int. Cl.
*A61M 16/20* (2006.01)
(52) U.S. Cl.
USPC .................................................. 128/205.13
(58) Field of Classification Search
USPC ............. 128/203.11, 205.24, 205.18, 205.14, 128/202.28, 202.29, 204.18, 203.28, 204.28, 128/205.13–18
See application file for complete search history.

(56) References Cited

U.S. PATENT DOCUMENTS 3,363,833 A * 1/1968 Laerdal ......................... 417/472
4,062,357 A 12/1977 Laerdal
4,532,923 A 8/1985 Flynn
5,121,745 A 6/1992 Israel
5,163,424 A 11/1992 Køhnke
5,295,478 A * 3/1994 Baldwin ................... 128/203.11
6,745,769 B2 6/2004 Klempau
8,042,536 B1 * 10/2011 Howey ..................... 128/203.15
2002/0108612 A1 8/2002 Klempau

FOREIGN PATENT DOCUMENTS

EP          0 367 285 A2   5/1990
WO       2006/091829 A2   8/2006

OTHER PUBLICATIONS

International Search Report for International Application No. PCT/IL2008/001338, mailed on Feb. 18, 2009, 3 pages.

* cited by examiner

*Primary Examiner* — Jackie Ho
*Assistant Examiner* — Mark Wardas
(74) *Attorney, Agent, or Firm* — Vorys, Sater, Seymour and Pease LLP; Susanne M. Hopkins; William L. Klima (57) ABSTRACT

A collapsible respiration bag assembly is disclosed and includes a flexible hollow body longitudinally extending about a longitudinal axis thereof between an air intake end and an air outlet end and formed with at least three annular folds. A patient valve is fitted at the outlet end and includes a face mask coupler transversing the longitudinal axis. An intake valve assembly is also included and a face mask fitted with a face engaging rim, a dome portion and a valve coupler detachably connectable to the face mask coupler. The dome portion of the face mask is deformable between an operative, concave position and a convex stowing position, where the dome portion is inverted and where the valve coupler is detached from the face mask coupler. The assembly is configurable between at least one extended, operative position and a fully collapsed stowed position where the annular fold zones at least partially overlap.

19 Claims, 11 Drawing Sheets

RESPIRATION BAG

This is a National Phase Application filed under 35 U.S.C. 371 as a national stage of PCT/IL2008/001338, filed on Oct. 7, 2008, claiming the benefit under 35 U.S.C. 119(e) of U.S. Provisional Application No. 60/960,667, filed on Oct. 9, 2007, the content of each of which is hereby incorporated by reference in its entirety.

FIELD OF THE INVENTION

The present invention is generally in the field of respiration bags and more particularly it is directed to compactable respiration bags. Such bags are often referred to also as resuscitators, artificial respiration bags, bag valve masks, etc.

BACKGROUND OF THE INVENTION

A respirator bag is a device using positive pressure to inflate the lungs of an unconscious person who is not breathing or to support shallow ineffective spontaneous breathing, in order to keep him oxygenated and alive. A hand-operable version comprises a face mask and a large hand-squeezed flexible bulb using ambient air, or with supplemental oxygen from a pressurized cylinder or the like.

Conventional artificial respiration bags have a cuff with which the artificial respiration bag is connected to an oxygen feed-line and with which it can be connected to a breathing mask, face mask, larynx tubus, pip-valve, etc.

The manually operated respiration bag is standard equipment in ambulances, operation and emergency rooms, first aid bags, civil and army medics, rescue units and the like.

It is an ever growing requirement to design respirator bags of compact size such that they can be easily carried by emergency professionals and such that a larger number of such units can be stored in a given space.

A variety of respirator bags and components used in conjunction therewith (face masks, one way valves, cuffs, etc.) are known in the art, for example:

U.S. Pat. No. 5,295,478 discloses a mouth-to-mask resuscitator which can be carried in a person's pocket consisting of an oronasal mask and a check valve which is inserted into the mask and allows a person to administer artificial ventilation to fill the victim's lung with air and to allow the victim to exhale air through an exit in the valve assembly away from the person administering the resuscitation. The mask is foldable into itself to form a cavity for storing the check valve which has inspiratory and exhalation air flow back pressures.

U.S. Pat. No. 5,163,424 discloses a disposable resuscitator including an elongated, elastically compressible squeeze bag having a first opening, a one-way valve for the intake of oxygen-containing gas into the bag mounted on the first opening, a second opening which is in airtight communication with a valve housing in the form of a transparent pipe having a pipe stub for the attachment of the resuscitator to a facial mask, and an outlet for exhalation air, the tubular valve housing containing a valve including a valve seat and a disc-shaped valve body of an elastomeric material and to having a centrally mounted, projecting guide pin which is axially displaceable in a hole in the valve seat, a body having a central passage forming the outlet for exhalation air being provided in the free end of the transparent pipe, the central passage being surrounded by an annular bead which is located coaxially and in contact with the valve member, the pipe stub for the attachment of the resuscitator to a facial mask extending from the side of the transparent pipe and being in communication with the zone located between the valve member and the body located in the free end of the transparent pipe.

U.S. Pat. No. 6,745,769 is concerned with a respiration bag having at least one connecting stub, the respiration bag comprising: a bag-shaped hollow body defining a longitudinal axis having a direction; at least one fold region extending annularly over said body; said bag-shaped body being foldable in the direction of said longitudinal axis from a first stable position wherein said hollow body extends smoothly over said fold region to a second stable position wherein said bag-shaped body is bent inwardly in the direction of said axis at said fold region to define an annular fold in said fold region; and, holding means for responding to pressure within said bag-shaped hollow body to hold said hollow body in said second stable state during operational use of said respiration bag.

U.S. Pat. No. 5,121,745 discloses a disposable self-inflatable rescue mask comprising a transparent, flexible form-retaining plastic dome-shaped foldable portion having around its peripheral edge an inflatable bladder provided with a built-in self-sealing air valve, which allows the ambient air to flow into the inflatable bladder and self-seals the air in the self-inflated mask which retains its shape firmly, said bladder being shaped to fit around the nose and mouth areas, and effectively seal against the patient's face; and a blow-in tube disposed in an opening at the apex of the dome is provided with a mouthpiece for delivery of expired air to the patient. The mask is packaged in a carrying case comprising two similar parts to form a container which is shaped to receive said deflated mask in a flattened and folded state, and sealed with a closure means.

U.S. Pat. No. 4,532,923 discloses a manually operable resuscitator bag of one-piece construction having a generally elongated football shape, an inlet at one said end, and an outlet at the other end, fold-rings in each end portion having walls of reduced thickness, whereby the ends may be telescoped, ridges of thickened wall section between the fold-rings, the center of the bag having a wall thickness equal to the thickness of said ridges in the tapering ends between the fold-rings, and longitudinal ribs formed on the outer surface of the center of the bag spaced around the circumference, providing increased resiliency and a rapid recovery for the shape of the bag.

U.S. Pat. No. 4,062,357 relates to a disposable respirator mask.

SUMMARY OF THE INVENTION

The present invention is directed to a collapsible respiration bag assembly comprising a face mask and being displaceable between at least one extended, operative position and a fully collapsed storage position, though readily available for deployment into the operative, extended position.

According to the invention there is provided a collapsible respiration bag assembly comprising a flexible hollow body longitudinally extending about a longitudinal axis thereof between an air intake end and an air outlet end and formed with at least three annular fold zones; and a patient valve fitted at said outlet end and comprising a face mask coupler transversing said longitudinal axis; an intake valve assembly; a face mask fitted with a face engaging rim, a dome portion and a valve coupler detachably connectable to said face mask coupler; said dome portion being deformable between an operative, concave position and a convex stowing position, where said dome portion is inverted and where said valve coupler is detached from said face mask coupler; said assembly being configurable between at least one extended, operative position and a fully collapsed stowed position where the at least three annular fold zones at least partially overlap.

The flexible hollow body collapses in a bellows-type arrangement ('accordion') such that several fold zones at least partially overlap.

According to a particular embodiment of the invention the intake valve assembly is a substantially flat body formed with a confined flow space extending between a front plate and a rear plate; and the thickness of said intake valve assembly does not exceed about 10 mm.

According to a design of the invention the intake valve assembly comprises a first check valve facilitating ambient air flow into the confined flow space, a discharge check valve to facilitate flow from said confined flow space to the environment upon pressure rise within said confined flow space beyond a predetermined pressure threshold, a reservoir coupler for connecting an oxygen reservoir bag, an oxygen coupler for attaching to an oxygen supply line, and a second inlet check valve to facilitate air flow in direction from the confined flow space into flexible hollow body.

Any one or more of the following features and embodiments may be incorporated in the respiration bag and constitute an embodiment of the invention:

the valves of the intake valve assembly are flap-type valves (at times referred to as 'mushroom-type valves');
the front plate is formed with a depression for receiving a rearwards facing projection of the patient filter, at the fully collapsed stowed position;
the oxygen coupler is a flexible pipe stub radially extending from the confined flow space;
the oxygen coupler is a flexible pipe stub tangentially extending from the confined flow space; alternatively, the pipe stub projects radially therefrom. However, the tube does not protrude larger then valve, i.e. does not project from the perimeter of the intake valve assembly;
a diameter of an annular fold zone at the air intake end of the hollow body is designed to accommodate the intake valve assembly with at least a portion of a flexible pipe stub extending from the confined flow space at least partially coiled over said intake valve assembly;
at the stowed position the valve coupler of the face mask is received within a valve coupler receptacle of the patient valve;
at the stowed position the intake valve and the face mask are fully received within the collapsed hollow body;
the hollow body is readily available for deployment into the operative, extended position by puling the air intake end and the air outlet end at opposite directions;
at the fully collapsed, stowing position the thickness of the assembly does not exceed about 55 mm
at the fully collapsed, stowing position the thickness of the assembly does not exceed the combined thickness of the intake valve assembly and the patient valve;
at the fully collapsed, stowing position the thickness of the assembly does not exceed that that of a central annular fold zone of the hollow body;
the reservoir coupler is fitted with a collapsible support element for maintaining a free flow path between an opening of the reservoir bag and the reservoir coupler;
the hollow body may be deployed into several different intermediate positions where a rear-most annular fold zone at the air intake end of the hollow body overlaps an adjoining annular fold zone, to thereby reduce the effective volume of the hollow body;
at the intermediate position an inside face of the rear-most annular fold zone overlaps a corresponding inside face of the adjoining annular fold zone;
at the intermediate position an outside face of the rear-most annular fold zone overlaps a corresponding outside face of the adjoining annular fold zone;
the face mask coupler substantially vertically extending with respect to the longitudinal axis of the hollow body;
an air flow path extends between the hollow body to the face mask coupler via an annular path of the patient valve, said annular path surrounding the valve coupler receptacle of the patient valve;
optionally the face mask/patient valve/flexible hollow body are transparent to facilitate inspection of operation of the valves and check for valve obstruction and to allow inspection of secretions from the patient;
the hollow body comprises 6 annular fold lines and 7 fold zones;
the hollow body has at least one partially collapsed though operative position wherein at least one annular fold zone is inverted and at least partially overlaps at least one other annular fold zone, wherein a volume within said hollow body is reduced though retaining elasticity of the hollow body to thereby spontaneously expand after manual squeeze thereof;
the patient valve comprises a coupler for detachably attaching thereto a peep valve;
a fastener is provided for securing the hollow body at a partially collapsed positions thereof;
at the operative position the valve coupler of the face mask extends before the face engaging rim whilst at the convex, stowing position the dome of the face mask is inverted such that the valve coupler extends after the face engaging rim;
the face mask may be detachably attached to the patient valve via a flexible, collapsible conduit in the form of a bellows-type pipe attached at one end to the patient valve and at an opposite end thereof it is attached to a coupler of the face mask;
at the stowed position the intake valve assembly and the patient valve at least partially overlap along the longitudinal axis of the device.

BRIEF DESCRIPTION OF THE DRAWINGS

In order to understand the invention and to see how it may be carried out in practice, embodiments will now be described, by way of non-limiting examples only, with reference to the accompanying drawings, in which:

FIGS. 5A to 5D are respective views of the respiration bag at a fully collapsed, stowed position, wherein:

DETAILED DESCRIPTION OF EMBODIMENTS

Figure 1:
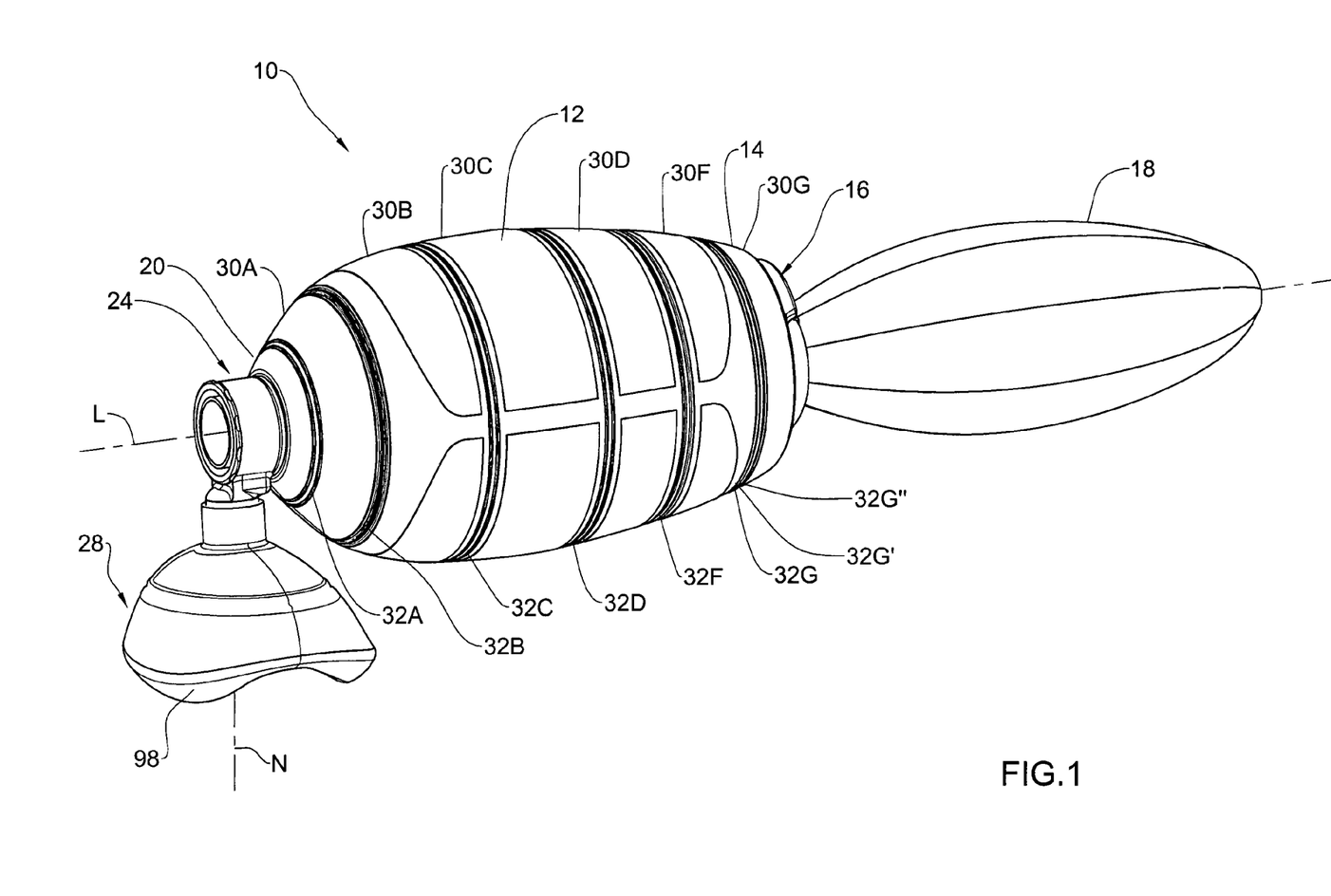
FIG. 1 is an isometric view of the respiration bag according to the present invention, fitted with an oxygen reservoir bag, at a fully extended, operative position.
Figure 2:
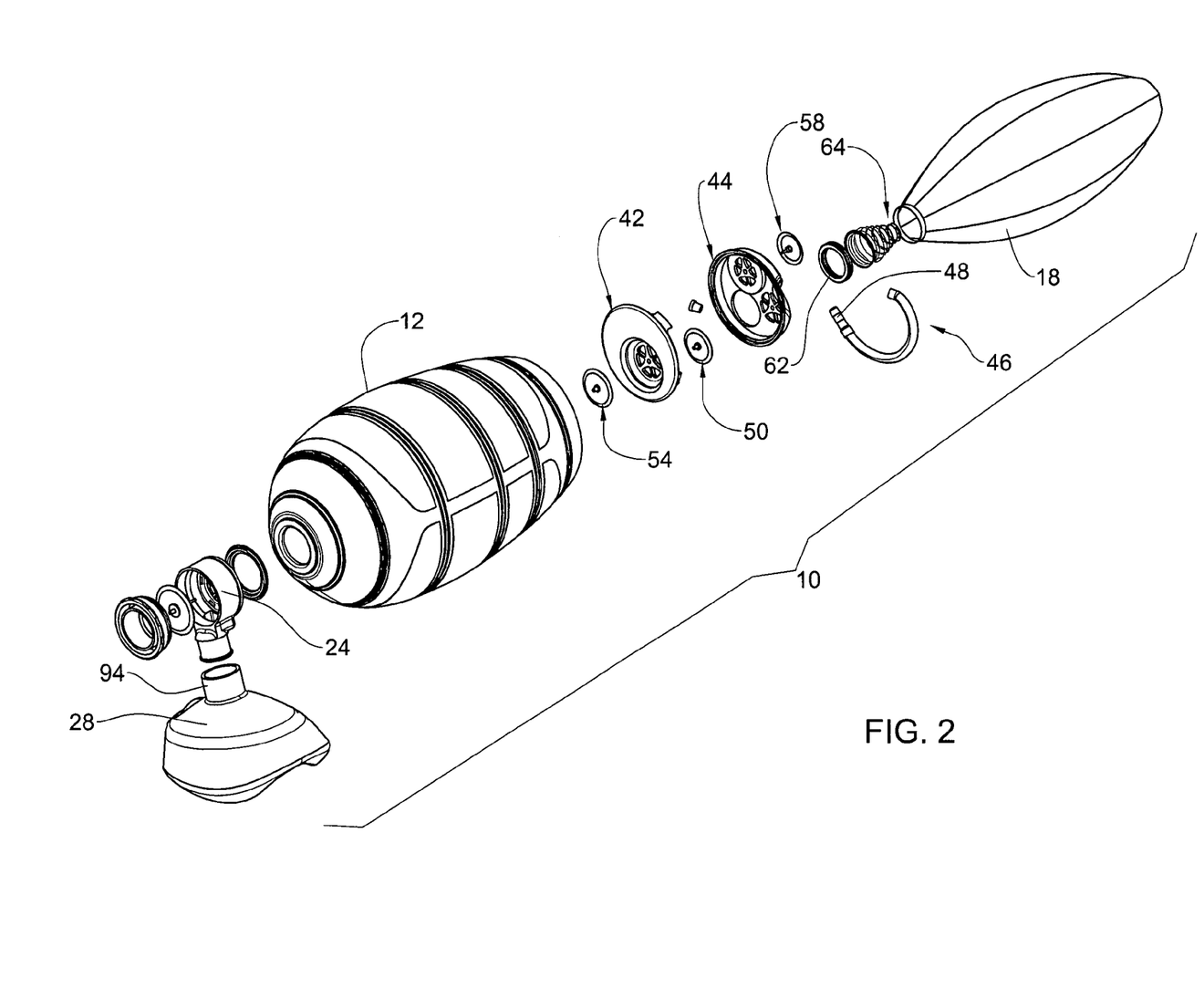
FIG. 2 is an exploded isometric view of the respiration bag of FIG. 1.
Figure 3:
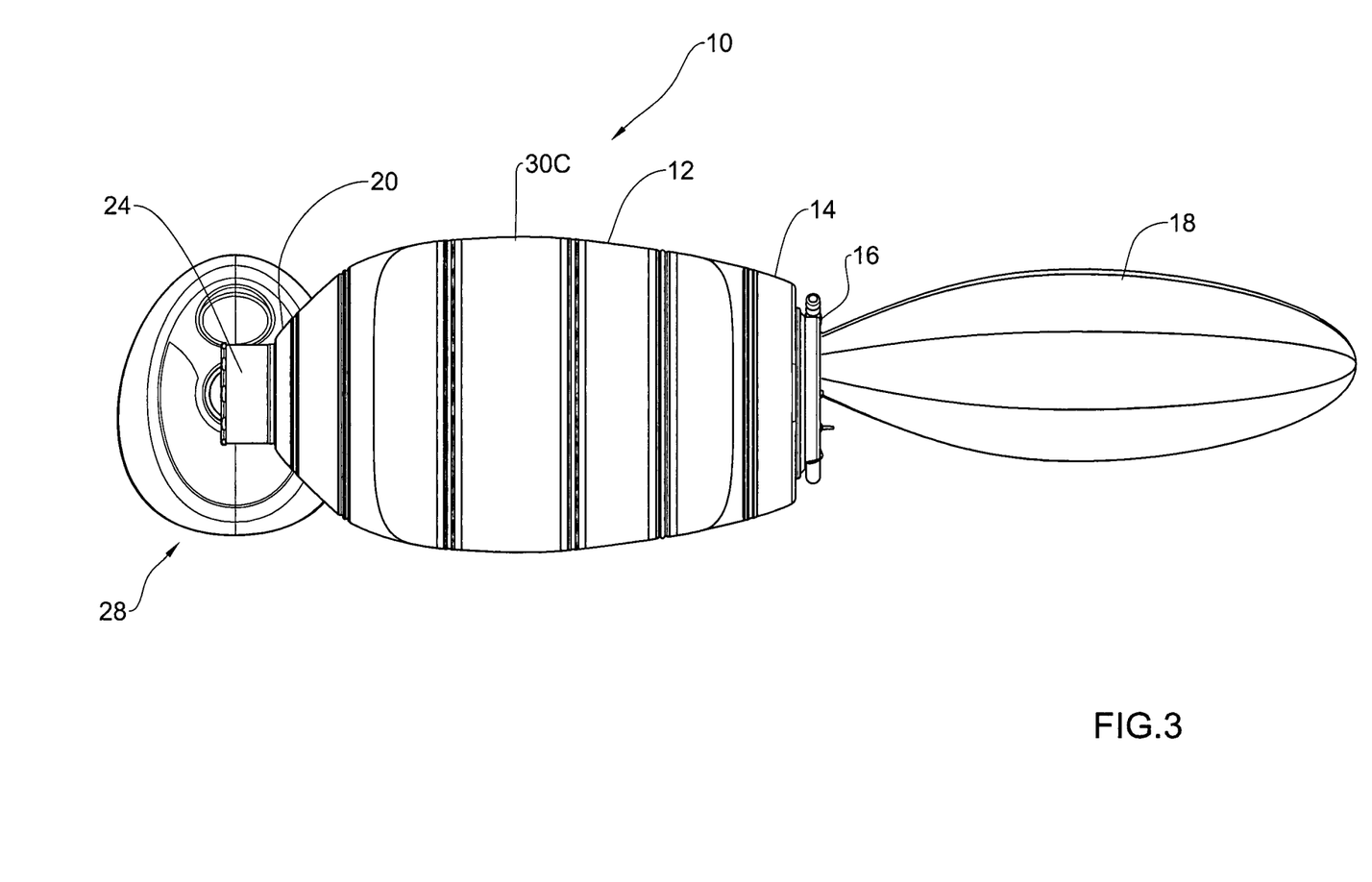
FIG. 3 is a top view of the respiration bag of FIG. 1.

Attention is first directed to FIGS. 1 to 3 of the drawings illustrating a collapsible respiration bag in accordance with the present invention generally designated 10 comprising a flexible hollow body 12 extending between an air intake end 14 fitted with an intake valve assembly generally designated 16, and a air outlet end generally designated 20. Attached to the intake valve assembly 16 there is an oxidation reservoir bag 18 and the air outlet end 20 is fitted with a patient valve designated 24 to which is detachably attached a face mask generally designated 28.

Figure 7A:
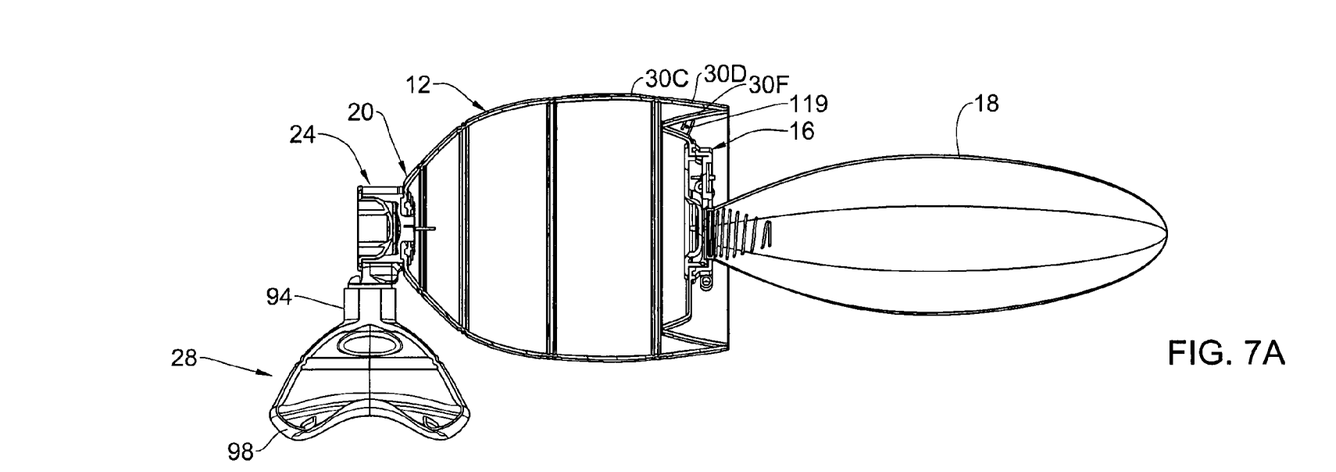
FIG. 7A is a side sectioned side view of the respiration bag in a second operative position, partially extended.
Figure 7B:
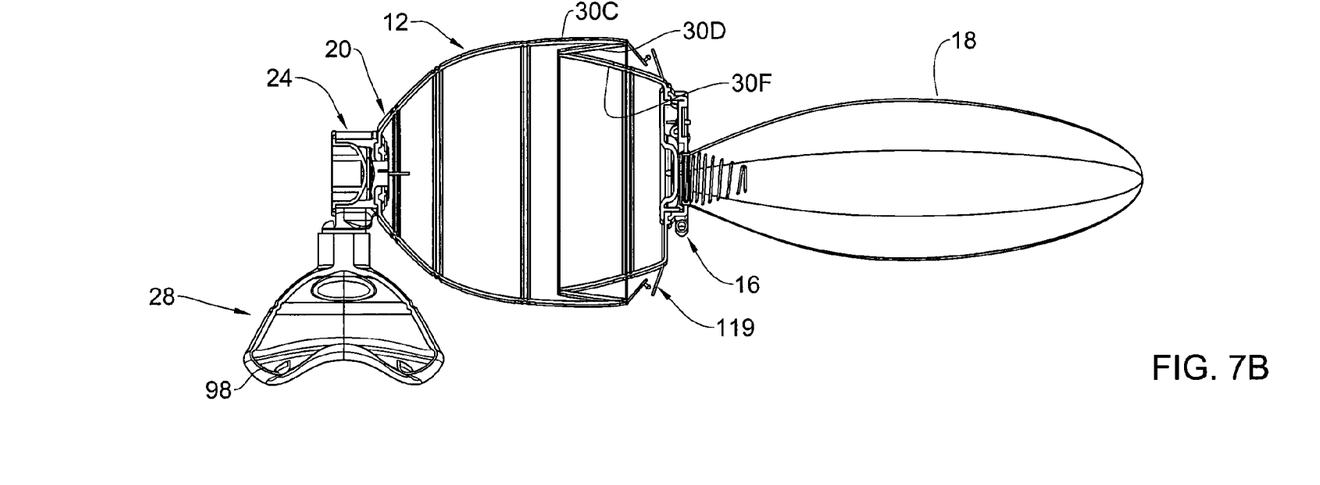
FIG. 7B is a side sectioned side view of the respiration bag in another operative position, partially extended

Flexible hollow body 12 longitudinally extends about a longitudinal axis L (FIG. 1) extending between the air intake end 14 and the outlet end 20. The hollow body is made of resilient material e.g. silicon rubber and is formed with a plurality of annular fold zones, 6 in the present example, designated 30A, 30B, 30C, 30D, 30F, and 30G integrally molded and enabling one another with an intermediate fold zone 32A, 32B, 32C, 32D, 32F and 32G, respectively, whereby the hollow bag may be collapsed into one or more other operative positions (FIGS. 5A to 5C) wherein the hollow body volume are into a fully collapsed stowed position (FIGS. 7A and 7B).

Deploying the hollow body 12 from either of its collapsed positions into its fully deployed position takes place by pulling the air intake end 14 and the air outlet end 20 in opposite directions along the longitudinal axis of the hollow body. Collapsing the hollow body into its partially collapsed, though operative positions takes place by gripping the hollow body 12 at its center and depressing the air intake end 14 in direction of the air outlet end 20, to the desired extent.

Figure 4A:
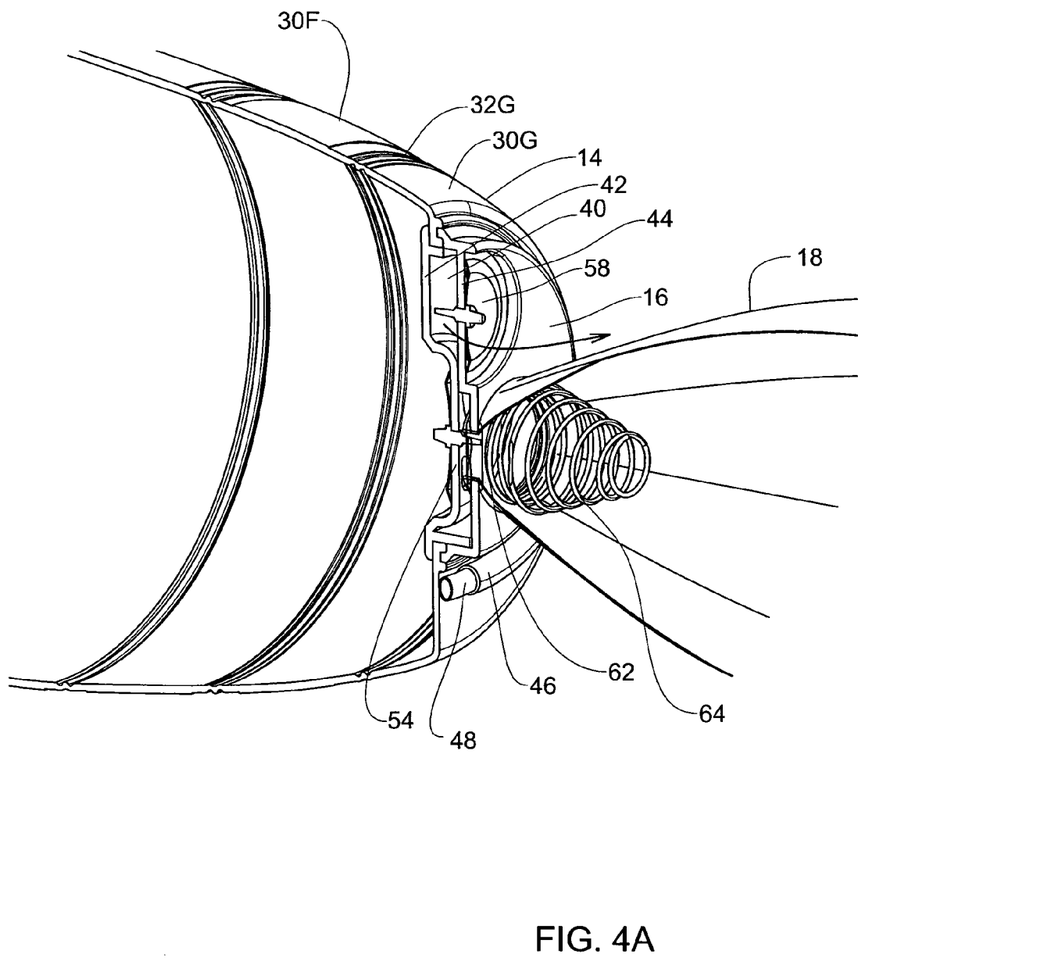
FIG. 4A is a sectioned, rear isometric view of an intake end of the respiration bag.
Figure 4B:
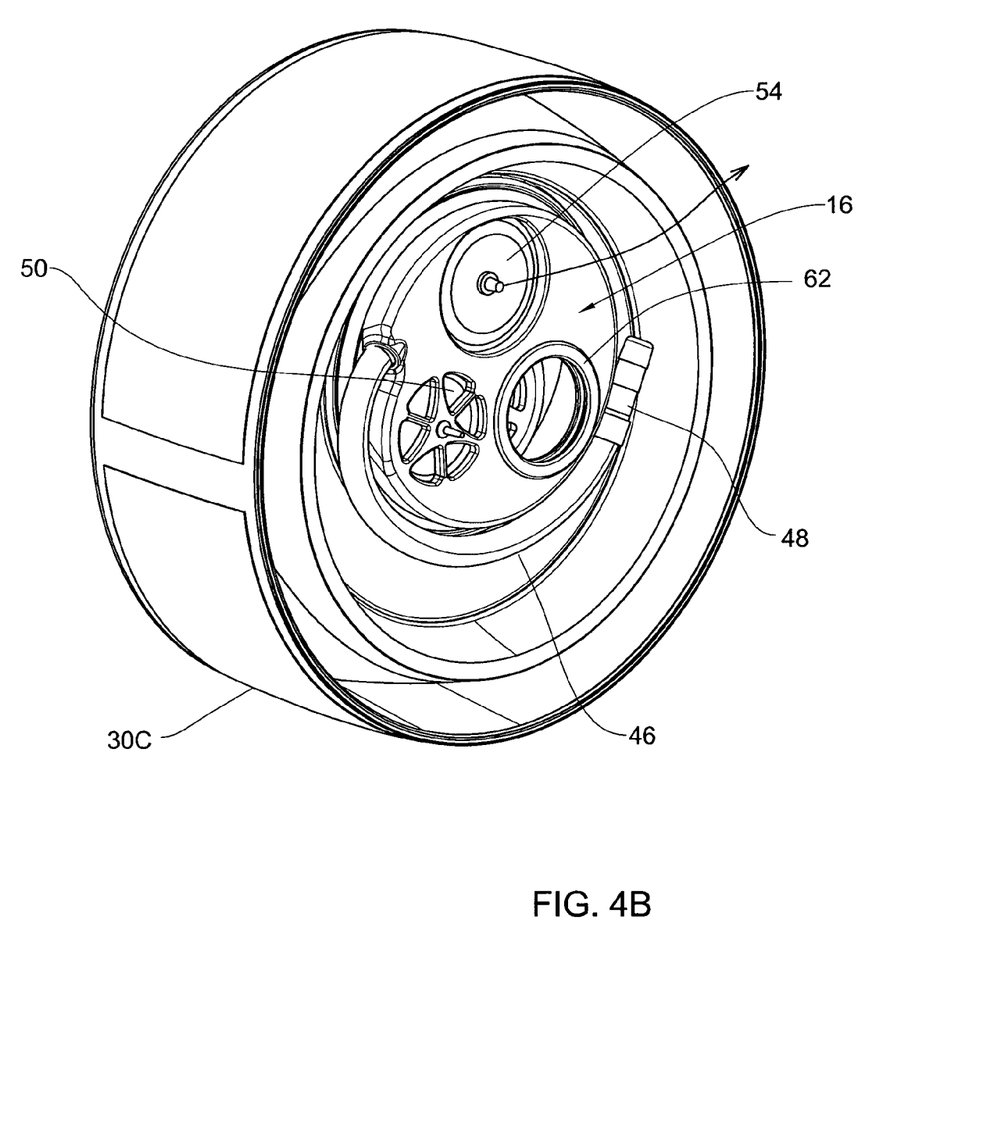
FIG. 4B is a rear isometric view of an intake end of the respiration bag.

Further attention is now made in particular to FIGS. 2 and 4A for better visualizing the air intake assembly 16. As can be seen, the intake valve assembly is a substantially flat body formed with a confined space 40 extending between a front plate 42 and a rear plate 44 valves fitted therein, as will follow. Extending into the confined space 40 there is oxygen (or other breathing air supply line) in the form of a tangentially extending type tube 46 fitted at its end with a stub 48 for coupling to an oxygen supply line. The tube 46 is flexible and is coiled about the intake valve assembly 16 such that it does not project from the overall size of the intake valve assembly and also from the collapsed state of the respiration bag, e.g. as in FIG. 4B, the tube 46 does not extend from the intake valve assembly 16 or the hollow body boundaries.

The intake valve assembly 16 comprises an array of check valves comprising in turn an ambient air intake valve 50 fitted on the rear plate 44 and adapted for facilitating ingress of ambient air into the confined space 40. An inlet valve 54 is fitted on the front plate 42 to facilitate airflow in a direction from the confined space 40 into the hollow body 12. A pressure threshold valve 58 is mounted on the rear plate 44 designed to discharge oxygen or other pressurized gas introduced into the confined space 40 through the gas supply tube 46, in case of pressure exceed within the confined space 40. A reservoir coupler 62 is fitted on the rear plate 44 for connecting thereto the oxygen reservoir bag 18 with a free flow passage extending between the oxygen reservoir bag 18 and the confined space 40 via the coupler 62.

In order to retain a free flow path between the oxygen reservoir bag 18 and the confined space 40 there is provided a collapsible support element in the form of a coiled spring 64 which prevents unintentional collapse of the reservoir bag 18 which in this case may block the passage into the confined space 40.

Figure 6:
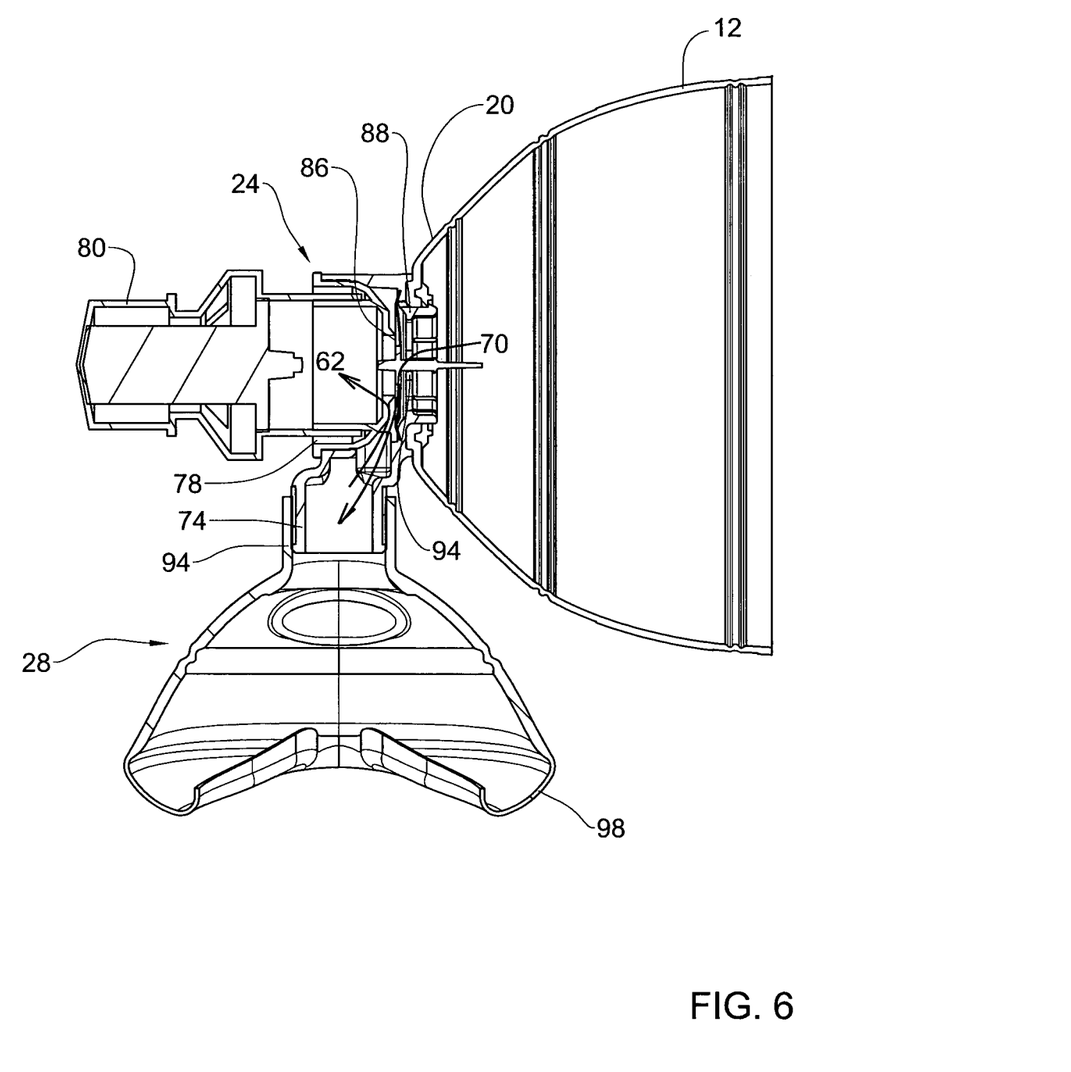
FIG. 6 is a sectioned view of a side portion of the respiration bag, the patient valve fitted with a peep valve.

The patient valve 24 fitted at the air outlet end 20 is a one-way valve allowing air flow from the hollow body 12 towards the patient, only in direction of arrow 70 in FIG. 6. The patient valve 24 is fixedly attached at the air outlet end 20 of the hollow body 12. The patient valve 24 comprises a coupler 74 for detachably attaching thereto the face mask 28 in a fit connection or a snip type connection such that the face mask 28 remains attached to the assembly during operation thereof, however it can readily be detached for stowing, as will be explained hereinafter. It is noticed that the face mask coupler 74 extends in a direction of axis N (FIG. 1), substantially transversing the longitudinal axis L of the hollow body. The patient valve 24 is further formed with an annular coupler at 78 for detachably attaching thereto a peep valve 80 (FIG. 6) useful in lung failure and other medical situations for increasing the outlet force required to exhale through the patient's The patient valve 24 comprises a flexible diaphragm 84 deformable between an inhaling position upon squeezing the hollow body 12 and an exhaling position upon expansion of the hollow body 12 and exhale of air from the patient (not shown). In the inhaling position the diaphragm 84 deforms against an annular valve seat 86 (FIG. 6) allowing air flow in direction of arrow 70 whilst the exit through the coupler 78 is sealed. However, in the exhaling position the diaphragm 84 deforms to seal against seating 88 thereby presenting airflow in a direction opposite to arrow 70 rather facilitating airflow in the direction of arrow 92 e.g. to the surroundings or out through the peep cells 80.

Figure 5A:
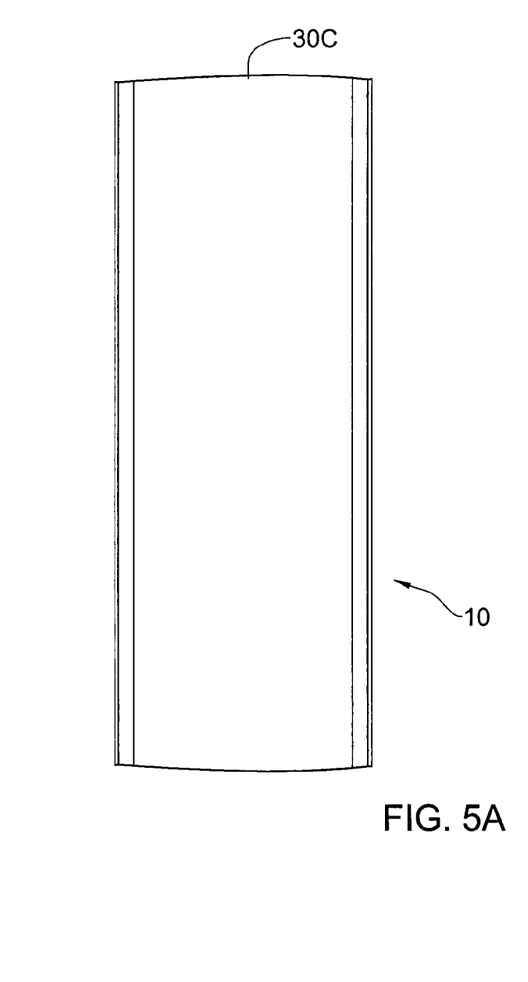
FIG. 5A is a side view of the respiration bag at a fully collapsed, stowed position.
Figure 5B:
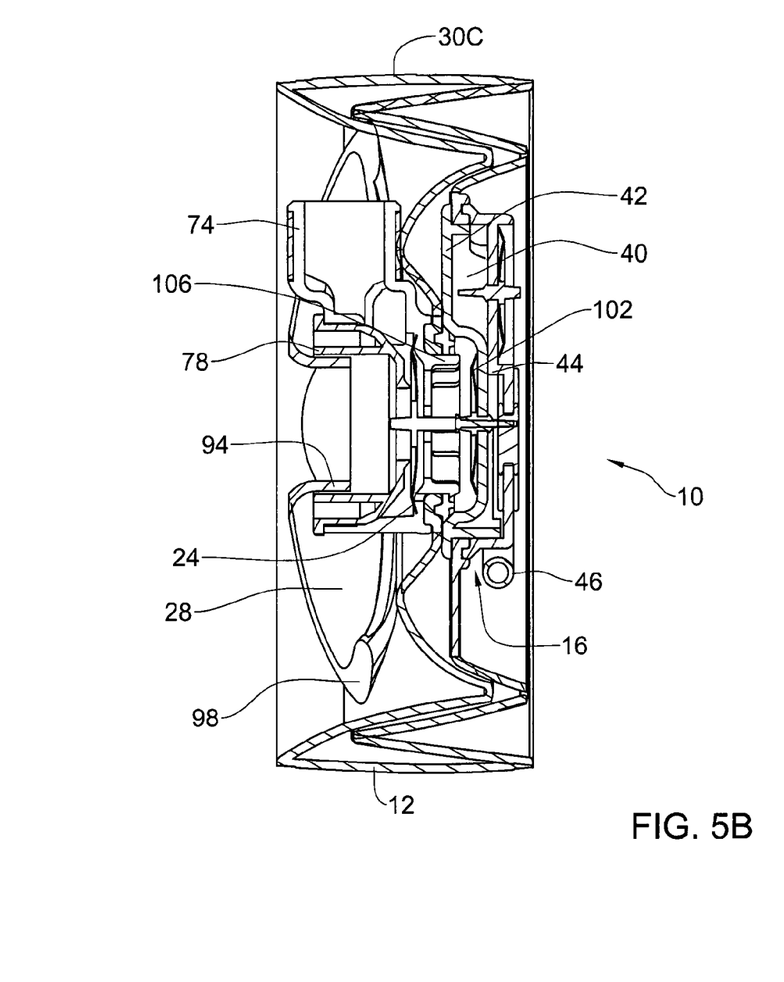
FIG. 5B is a cross-sectioned side view of the respiration bag of FIG. 5A.
Figure 5C:
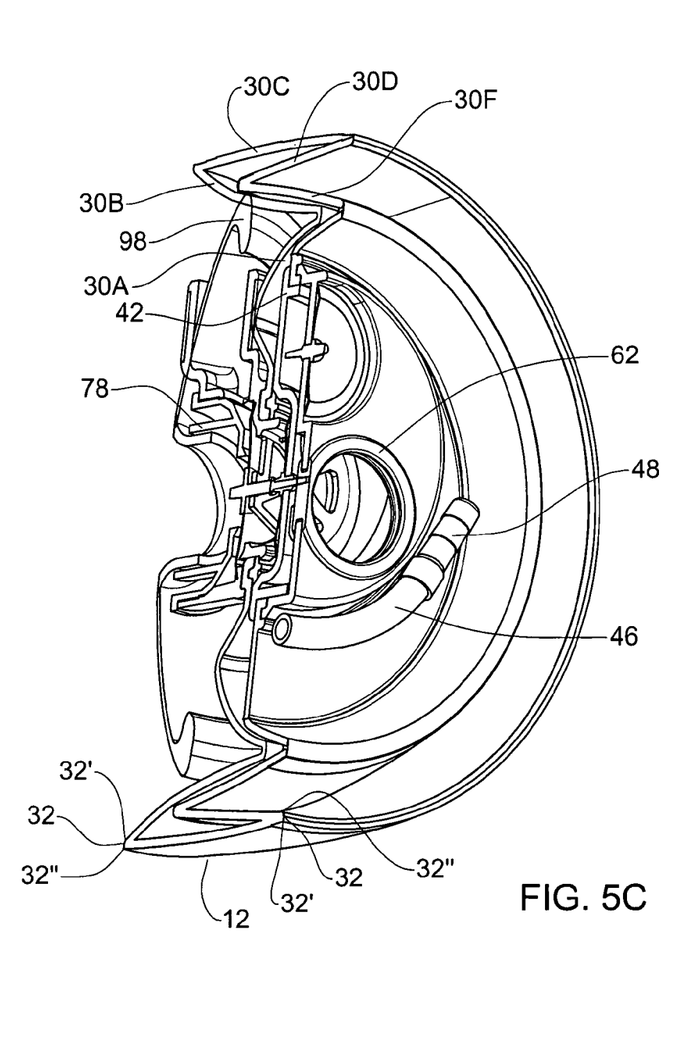
FIG. 5C is a rear sectioned isometric view of the respiration bag of FIG. 5A.
Figure 5D:
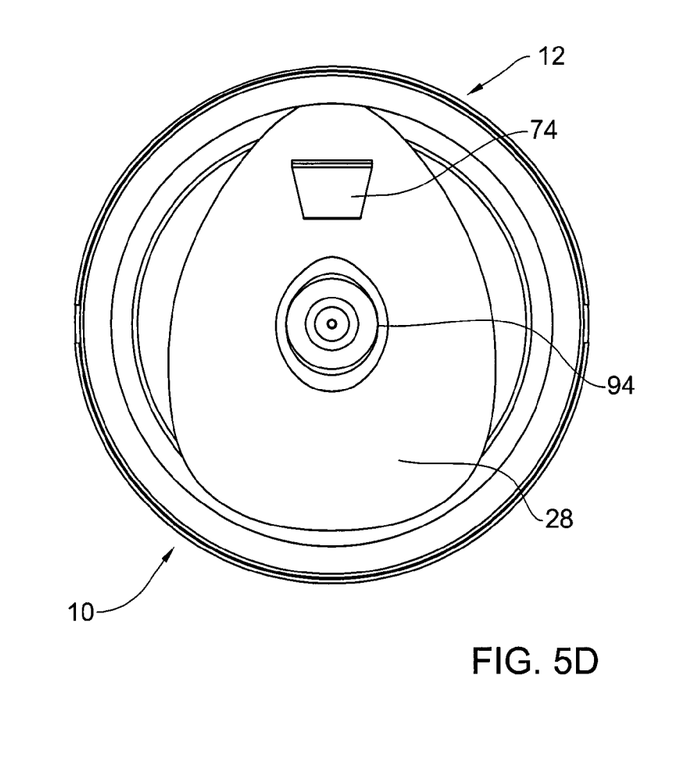
FIG. 5D is a front view of the respiration bag of FIG. 5A.

The inner diameter of the coupler 78 is sized so as to comfortably accommodate a corresponding coupler 94 of the face mask 28 as can be seen in FIGS. 5B and 5C.

The face mask 28 is formed of a resilient material such as silicon rubber and comprises a valve coupler 94 for pressed fit over the face mask coupler 74 of the patient's valve 24. Its opposite edge is formed with a face engaging rim 98 designed for soft and sealing engagement with a patient's nose and mouth (not shown). The arrangement is such that the dome portion of the face mask is deformable between an operative, concave position as in FIGS. 1, 2, 3, 6, 7A and 7B, and wherein the face engaging ring 98 extends in continuation below the valve coupler 94, and a convex, stowing position (FIGS. 5B and 5C) wherein the face engaging ring 98 extends before the valve coupler 94, wherein the face mask is designed to occupy a minimum space for conveniently stowing within the collapsed hollow body as seen in FIGS. 5B and 5C wherein the face mask 28 does not project from the collapsed hollow body 12.

As can further been seen in particular in FIGS. 5B and 5C, the front plate 42 of the intake valve assembly 16 is formed with a rearwardly facing depression at 102 fitted for receiving a rearward projection 106 of the patient valve 24 whereby at the fully collapsed position, the intake valve assembly 16 and the patient valve 24 are adjoining one another, such that they are well received within the collapsed hollow body 12 and do not project therefrom. It is thus noted that at the stowed position the intake valve assembly 16 and the patient valve 24 at least partially overlap along the longitudinal axis L of the device.

As can be seen in FIGS. 5B and 5C, at the fully collapsed position, the respiration bag assembly 10 assumes a thickness which substantially corresponds with the width of the central annular fold zone 30C with overlapping of neighboring annular fold zones. As mentioned hereinbefore, in this position the intake valve assembly 16 and the patient valve 24 are fully received within the collapsed hollow body and do not exceed beyond the collapsed width being in the range of about 50-70 mm, and by a particular embodiment does not exceed about 55 mm.

Turning now to FIGS. 7A and 7B, the respiration bag assembly is illustrated in two different operative positions, partially collapsed and useful for obtaining a smaller effective volume of the resuscitator. In FIG. 7A, the hollow bag is collapsed in a first respective position wherein an inside face of the rear-most annular fold zone 30F overlaps a corresponding inside face of the adjoining annular fold zone 30D whereby the volume of the partially collapsed hollow bag is now reduced by about 25% useful for resuscitation of youngsters and the like. However, the volume can be designed to suit different requirements.

In the embodiment of FIG. 7B an outside face of the rear-most annular fold zone 30F overlaps a corresponding outside face of the adjoining annular fold zone 30D, both being partially in overlap relation with the central fold zone 30C. In this position, the effective squeezing volume of the hollow body 12 is even more reduced, thereby useful for toddlers and the like.

As can further be seen in FIGS. 7A and 7B, in order to maintain the hollow body at its partially collapsed position, there is fitted a locking mechanism designated 119 e.g. in the form of a Velcro™ fastener, magnetic fastener, snap-type fastener, etc.

Converting the respiration bag 10 into its collapsed, stowed position takes place by detaching the face mask 28 from the face mask coupler 74, collapsing the bag 12 by compressing the air intake end 14 towards the air outlet end 20 along the longitudinal axis extending therebetween, in a bellows-type fashion, to thereby obtain a compact size of the bag corresponding with the width of the central annular fold zone (FIG. 5A). Then the face mask 28 is inverted by deforming the dome over the valve coupler 94 and introducing the valve coupler 94 into the receptacle of the coupler 78 of the patient valve 24.

Deploying the respiration bag 10 into its operative position (e.g. FIG. 1) is carried out at a reverse sequence of operations.

It is further appreciated that any of the components of the assembly may be transparent to provide inspection and visualizing of the operating components thereof and to identify secretions from the patient.

The valves illustrated in the figures and as discussed hereinbefore are flap-type valves useful for obtaining a substantially small dimensioned device, in particular at its folded position.

The structure and design of the hollow bag is such that it spontaneously tends to maintain its expanded position whereby upon squeezing the air within the hollow bag is forced through the patient valve assembly 24 (at this position air cannot escape through the air intake assembly owing to the one-way inlet valve 54). However, upon ceasing the squeezing pressure from the hollow body, it will spontaneously retain its expanded position this time drawing air through the inlet valve assembly 16 however, without drawing air or secretions from the patient through valve assembly 24.

It is further noticed that one or more of the intermediate fold zone 32A, 32B, 32C, 32D, 32F and 32G are in the form of double annular rims (as seen for example in FIGS. 1 and 5C and represented by reference numerals 32' and 32", respectively), such that even after several years of the device being at the stowed position, the ribs will still have their resilience to bounce and allow the hollow body to act as a pump.

Figure 8A:
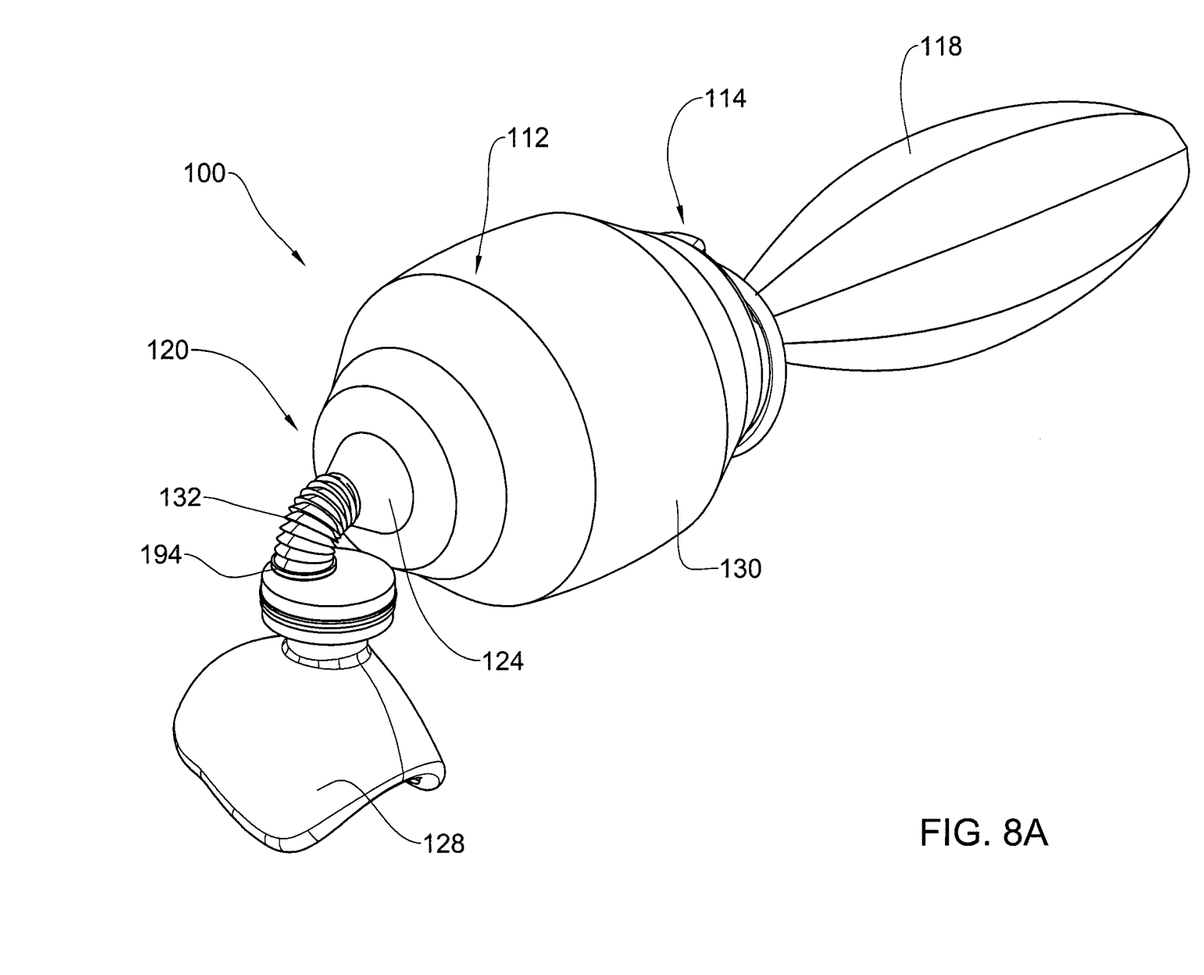
FIGS. 8A and 8B illustrate a modification of a respiration bag according to the present invention, at an expanded position and a collapsed position, respectively.
Figure 8B:
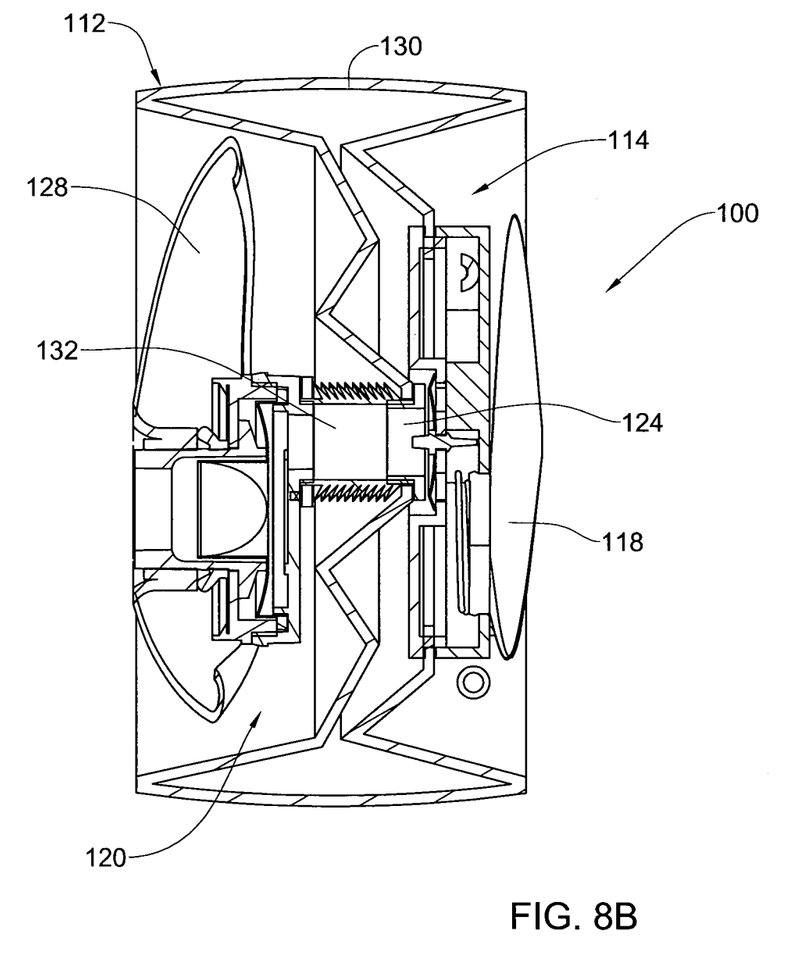

Turning now to the embodiment of FIGS. 8A and 8B, there is illustrated a collapsible respiration bag in accordance with a further embodiment of the present invention, generally designated 100 and having a flexible hollow body 112 of similar construction as discussed in connection with the previous embodiments, extending between an air intake end 114 and a air outlet end generally designated 120. Attached to an intake valve assembly there is an oxidation reservoir bag 118. An air outlet end 120 is fitted with a patient valve designated 124.

In this embodiment, a face mask 128 (which is also similar to the face mask previously discussed) is detachably attached to the patient valve 124 via a flexible, collapsible conduit 132 which in the present example is a bellows-type pipe attached at one end to the patient valve 124 and at an opposite end thereof it is attached to a coupler 194 of the face mask 128.

The arrangement is such that the respiration bag 100 is readily deployable from its fully collapsed position (FIG. 8B) into its operative position (fully or partially deployed; e.g. FIGS. 7a and 7B), merely by pulling at opposite ends of the device and where the face mask 128 is placed over a patients face and the respiration bag can be easily manipulated.

It is noted that in the collapsed position (FIG. 8B) the collapsible conduit 132 is in its collapsed, compact position allowing for the entire devise to retain a small and compact size which substantially does not exceed the width of the central annular fold zone 130.

Those skilled in the art to which this invention pertains will readily appreciate that numerous changes, variations and modifications can be made without departing from the scope of the invention mutatis mutandis.

The invention claimed is:

1. A collapsible respiration bag assembly comprising a flexible hollow body longitudinally extending about a longitudinal axis thereof between an air intake end and an air outlet end and formed with at least three annular folds; and a patient valve fitted at the outlet end and comprising a face mask coupler transversing the longitudinal axis; an intake valve assembly; a face mask fitted with a face engaging rim, a dome portion and a valve coupler detachably connectable to the face mask coupler; the dome portion being deformable between an operative, concave position and a convex stowing position, where the dome portion is inverted and where the valve coupler is detached from the face mask coupler; the assembly being configurable between at least one extended, operative position and a fully collapsed stowed position where the at least three annular fold zones at least partially overlap, wherein the face mask is configured for stowing within the collapsed flexible body when in its stowing position.

2. The collapsible respiration bag assembly according to claim 1, wherein the intake valve assembly is a substantially flat body formed with a confined flow space extending between a front plate and a rear plate, and fitted with an array of valves.

3. The collapsible respiration bag assembly according to claim 2, wherein the front plate is formed with a depression for receiving a rearwards facing projection of the patient valve, at the fully collapsed stowed position.

4. The collapsible respiration bag assembly according to claim 2, wherein the valve array of the intake valve assembly comprises a first check valve facilitating ambient air flow into the confined flow space, a discharge check valve to facilitate flow from the confined flow space to the environment upon pressure rise within the confined flow space beyond a predetermined pressure threshold, a reservoir coupler for connecting an oxygen reservoir bag, an oxygen coupler for attaching to an oxygen supply line, and a second inlet check valve to facilitate air flow in direction from the confined flow space into flexible hollow body.

5. The collapsible respiration bag assembly according to claim 4, wherein the oxygen coupler is a flexible pipe stub tangentially extending from the confined flow space.

6. The collapsible respiration bag assembly according to claim 4, wherein a diameter of an annular fold zone at the air intake end of the hollow body is designed to accommodate the intake valve assembly with at least a portion of a flexible pipe stub extending from the confined flow space at least partially coiled over the intake valve assembly.

7. The collapsible respiration bag assembly according to claim 4, wherein at the stowed position the valve coupler of the face mask is received within a valve coupler receptacle of the patient valve.

8. The collapsible respiration bag assembly according to claim 1, wherein at the stowed position the intake valve and the face mask are fully received within the collapsed hollow body.

9. The collapsible respiration bag assembly according to claim 1, wherein the hollow body is readily available for deployment into the operative, extended position by pulling the air intake end and the air outlet end at opposite directions.

10. The collapsible respiration bag assembly according to claim 1, wherein at the fully collapsed, stowing position a thickness of the assembly does not exceed about 55 mm.

11. The collapsible respiration bag assembly according to claim 1, wherein at the fully collapsed, stowing position a thickness of the assembly does not exceed that of a central annular fold zone of the hollow body.

12. The collapsible respiration bag assembly according to claim 1, wherein at the fully collapsed, stowing position a thickness of the assembly does not exceed the combined thickness of the intake valve assembly and the patient valve.

13. The collapsible respiration bag assembly according to claim 1, wherein the hollow body may be deployed into an intermediate position where a rear-most annular fold zone at the air intake end of the hollow body overlaps an adjoining annular fold zone, to thereby reduce the effective volume of the hollow body.

14. The collapsible respiration bag assembly according to claim 1, wherein the face mask coupler substantially vertically extending with respect to the longitudinal axis of the hollow body.

15. The collapsible respiration bag assembly according to claim 7, wherein an air flow path extends between the hollow body to the face mask coupler via an annular path of the patient valve, the annular path surrounding the valve coupler receptacle of the patient valve.

16. The collapsible respiration bag assembly according to claim 1, wherein the hollow body has at least one partially collapsed though operative position wherein at least one annular fold zone is inverted and at least partially overlaps at least one other annular fold zone, wherein a volume within the hollow body is reduced though retaining elasticity of the hollow body to thereby spontaneously expand after manual squeeze thereof.

17. The collapsible respiration bag assembly according to claim 1, wherein at the operative position the valve coupler of the face mask extends before the face engaging rim whilst at the convex, stowing position the dome of the face mask is inverted such that the valve coupler extends after the face engaging rim.

18. The collapsible respiration bag assembly according to claim 1, wherein the face mask may be detachably attached to the patient valve via a flexible, collapsible conduit in the form of a bellows-type pipe attached at one end to the patient valve and at an opposite end thereof it is attached to a coupler of the face mask.

19. The collapsible respiration bag assembly according to claim 1, wherein at the stowed position the intake valve assembly and the patient valve at least partially overlap along the longitudinal axis of the device.

\* \* \* \* \*